(12) United States Patent
Wang et al.

(10) Patent No.: US 8,128,620 B2
(45) Date of Patent: Mar. 6, 2012

(54) IRRIGATED ABLATION ELECTRODE HAVING PROXIMAL DIRECTION FLOW

(75) Inventors: Huisun Wang, Maple Grove, MN (US); Jeremy Dando, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1148 days.

(21) Appl. No.: 11/939,195

(22) Filed: Nov. 13, 2007

(65) Prior Publication Data

US 2009/0125016 A1    May 14, 2009

(51) Int. Cl.
*A61B 18/14* (2006.01)
(52) U.S. Cl. .......................................... 606/41
(58) Field of Classification Search ............... 606/41
See application file for complete search history.

(56) References Cited

U.S. PATENT DOCUMENTS

| | | |
|---|---|---|
| 5,056,517 A | 10/1991 | Fenici |
| 5,230,349 A | 7/1993 | Langberg |
| 5,334,193 A | 8/1994 | Nardella |
| 5,348,554 A | 9/1994 | Imran et al. |
| 5,423,811 A | 6/1995 | Imran et al. |
| 5,462,521 A | 10/1995 | Brucker et al. |
| 5,545,161 A | 8/1996 | Imran |
| 5,643,197 A | 7/1997 | Brucker et al. |
| 5,658,278 A | 8/1997 | Imran et al. |
| 5,697,927 A | 12/1997 | Imran et al. |
| 5,792,140 A | 8/1998 | Tu et al. |
| 5,843,152 A | 12/1998 | Tu et al. |
| 5,893,884 A | 4/1999 | Tu |
| 5,913,856 A | 6/1999 | Chia et al. |
| 5,919,188 A | 7/1999 | Shearon et al. |
| 6,015,407 A | 1/2000 | Rieb et al. |
| 6,017,338 A | 1/2000 | Brucker et al. |
| 6,120,476 A | 9/2000 | Fung et al. |
| 6,171,275 B1 | 1/2001 | Webster, Jr. |
| 6,217,576 B1 | 4/2001 | Tu et al. |
| 6,602,242 B1 | 8/2003 | Fung et al. |
| 6,611,699 B2 | 8/2003 | Messing |
| 6,942,661 B2 | 9/2005 | Swanson |

(Continued)

FOREIGN PATENT DOCUMENTS

WO    2005/048858 A1    6/2005

OTHER PUBLICATIONS

Wittkampf, et al., Radiofrequency Ablation with a Cooled Porous Electrode Catheter, JACC vol. 11, No. 2, Feb. 1988: 17A Abstracts.
Wittkampf, et al., Saline-Irrigated Radiofrequency Ablation Electrode with External Cooling, Journal of Cardiovascular Electrophysiology, vol. 16, No. 3, Mar. 2005.

(Continued)

*Primary Examiner* — Lee Cohen
(74) *Attorney, Agent, or Firm* — Dykema Gossett PLLC

(57) ABSTRACT

The present invention relates to improved ablation electrodes and catheter assemblies, as well as methods useful in conjunction with irrigated ablation catheters. Embodiments of the present invention further relate to an irrigated catheter having irrigation fluid directed at target areas where coagulation is more likely to occur to help minimize blood coagulation and the associated problems. The present invention further relates to an ablation electrode having an outer body with a proximal portion and a distal portion an inner cavity and at least one passageway that extends to an opening on the outer surface of the electrode, wherein the passageway is directed towards the proximal portion and/or proximal end of the electrode forming an acute angle with a longitudinal axis of the electrode.

17 Claims, 3 Drawing Sheets

U.S. PATENT DOCUMENTS

| | | |
|---|---|---|
| 7,166,105 B2 | 1/2007 | Mulier et al. |
| 7,815,635 B2 * | 10/2010 | Wittkampf et al. ............. 606/41 |
| 7,857,810 B2 * | 12/2010 | Wang et al. .................... 606/41 |
| 2005/0177151 A1 | 8/2005 | Coen et al. |
| 2007/0156131 A1 | 7/2007 | Datta |

OTHER PUBLICATIONS

Thomas, et al., A Comparison of Open Irrigated and Non-Irrigated Tip Catheter Ablation for Pulmonary Vein Isolation, Europace 6:330-335 (2004).

* cited by examiner

IRRIGATED ABLATION ELECTRODE HAVING PROXIMAL DIRECTION FLOW

BACKGROUND OF THE INVENTION a. Field of the Invention

The present invention relates to irrigated catheter assemblies. The present invention further relates to ablation electrodes and assemblies, including electrodes in which a proximal direction irrigation fluid flow is generated around the ablation electrode.

b. Background Art

Electrophysiology catheters are used for an ever-growing number of procedures. For example, catheters are used for diagnostic, therapeutic, and ablative procedures, to name just a few examples. Typically, a catheter is manipulated through the patient's vasculature and to the intended site, for example, a site within the patient's heart. The catheter typically carries one or more electrodes, which may be used for ablation, diagnosis, or other treatments.

There are a number of methods used for ablation of desired areas, including for example, radiofrequency (RF) ablation. RF ablation is accomplished by transmission of radiofrequency energy to a desired target area through an electrode assembly to ablate tissue at the target site. Because RF ablation may generate significant heat, which if not controlled can result in excessive tissue damage, such as steam pop, tissue charring, and the like, it is desirable to include a mechanism to irrigate the target area and the device with biocompatible fluids, such as saline solution. The use of saline irrigated ablation catheters can also prevent the formation of soft thrombus and/or blood coagulation.

Typically, there are two classes of irrigated electrode catheters, open and closed irrigation catheters. Closed ablation catheters usually circulate a cooling fluid within the inner cavity of the ablation electrode. Open ablation catheters typically deliver the cooling fluid through open outlets or openings on the surface of the electrode. Open ablation catheters use the inner cavity of the electrode, or distal member, as a manifold to distribute saline solution, or other irrigation fluids known to those skilled in the art, to one or more passageways that lead to openings/outlets provided on the surface of the electrode. The saline thus flows directly through the outlets of the passageways onto the distal electrode member. This direct flow through the distal electrode tip lowers the temperature of the distal tip during operation, often making accurate monitoring and control of the ablative process more difficult.

In general, open irrigated ablation catheters may improve the safety of radiofrequency catheter ablation by preventing protein aggregation and blood coagulation. A particular area of the electrode/catheter where the formation of coagulum or thrombus may occur during ablation procedures is at the proximal end of the electrode.

BRIEF SUMMARY OF THE INVENTION

The present invention is directed to improved ablation electrode assemblies and methods useful in conjunction with irrigated catheter devices and other ablation catheters. Embodiments of the present invention provide an irrigated catheter having irrigation fluid directed at target areas where coagulation is more likely to occur so as to minimize blood coagulation and associated problems.

The present invention relates to an ablation electrode for use with an irrigated ablation catheter. The electrode defines an outer body portion having an outer surface defining a proximal portion with a proximal end and a distal portion with a distal end. The electrode further includes an inner cavity defined by the outer body portion wherein the inner cavity includes a central longitudinal axis. The electrode further includes at least one passageway. The passageway extends from the inner cavity to the outer surface of the outer body portion of the electrode. The passageway extends from the inner cavity towards the proximal end of the electrode at an acute angle with respect to the central longitudinal axis of the inner cavity of the electrode. The proximal end of the electrode is typically where the electrode meets with the catheter shaft. It is commonly at this junction that coagulum and/or thrombus may form.

The present invention further provides another passageway that extends from the inner cavity towards the distal end of the electrode at an acute angle with respect to the central longitudinal axis of the inner cavity of the electrode.

The present invention further provides an ablation catheter assembly having an irrigated ablation electrode as described above coupled to or connected to a catheter shaft forming a catheter assembly. The present invention further provides an ablation system having an irrigated ablation electrode as described above coupled to or connected with a catheter shaft forming a catheter assembly in connection with a fluid source and an energy source.

The foregoing and other aspects, features, details, utilities, and advantages of the present invention will be apparent from reading the following description and claims, and from reviewing the accompanying drawings.

DETAILED DESCRIPTION OF THE INVENTION

In general, the instant invention relates to irrigated ablation electrode assemblies and to methods of using the irrigated ablation electrode assemblies in connection with catheter assemblies. For purposes of this description, similar aspects among the various embodiments described herein will be referred to by the same reference number. As will be appreciated, however, the structure of the various aspects may be different among the various embodiments.

Figure 1:
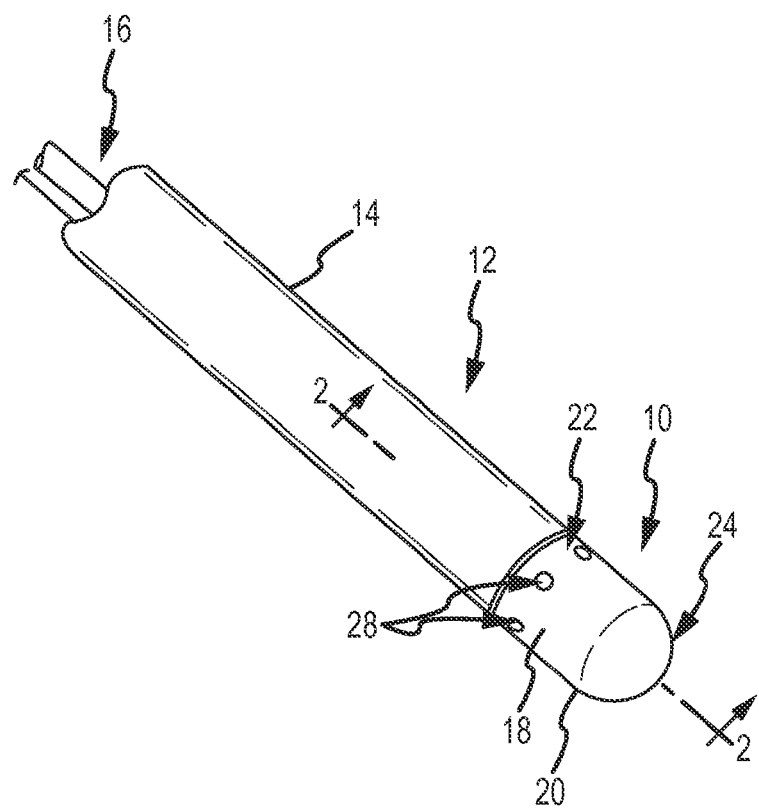
FIG. 1 is an isometric view of an ablation electrode according to an embodiment of the present invention.
Figure 2:
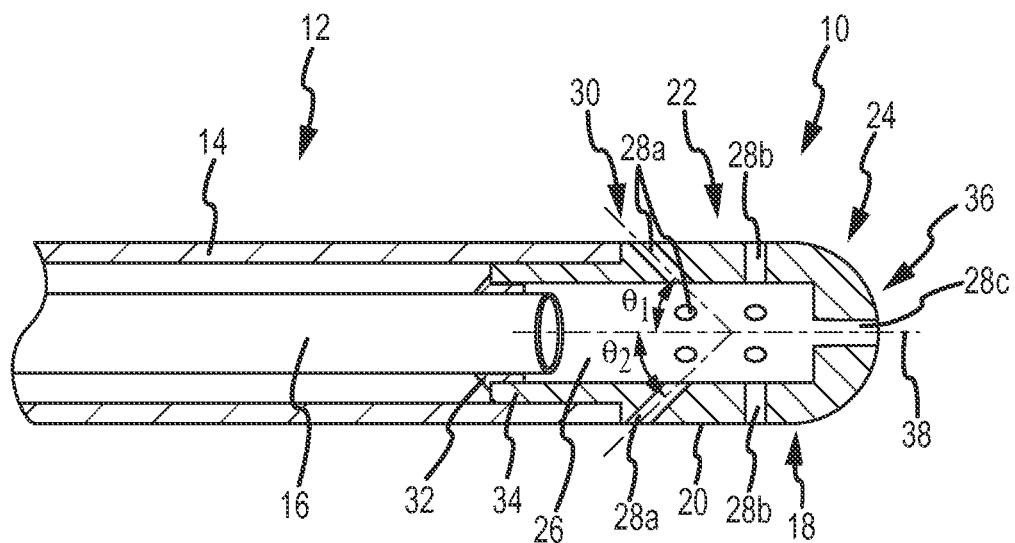
FIG. 2 is a cross-sectional view of an ablation electrode according to another embodiment of the present invention.

As generally shown in the embodiment illustrated in FIG. 1, the ablation electrode 10 may comprise part of an irrigated ablation catheter assembly 12. The present embodiments describe RF ablation electrodes and assemblies, but it is contemplated that the present invention is equally applicable to any number of other ablation electrodes and assemblies where the temperature of the device and the targeted tissue area may be factors during the procedure. FIGS. 2-3b, discussed in more detail below, illustrate ablation electrodes 10 according to alternate embodiments of the present invention.

In accordance with an embodiment, FIG. 1 is an isometric view of ablation electrode 10 connected to a catheter shaft 14 as part of irrigated ablation catheter assembly 12 having at least one fluid delivery tube 16 therein. The ablation electrode 10 is generally defined by an outer body portion 18 having an outer surface 20 and includes a proximal portion 22 and a distal portion 24. As further illustrated in FIG. 2, electrode 10 may further include an inner cavity 26 that may be coupled to or is in fluid communication with fluid delivery tube 16. Electrode 10 further includes at least one fluid or irrigation passageway 28 that extends from inner cavity 26 to outer surface 20 of electrode 10.

Electrode 10 is generally comprised of any electrically, and potentially thermally, conductive material known to those of ordinary skill in the art for delivery of ablative energy to target tissue areas. Examples of electrically conductive material include gold, platinum, iridium, palladium, stainless steel, and any mixtures thereof. A portion of electrode 10 is generally configured to be connected to or received by catheter shaft 14 of catheter assembly 12 therein coupling electrode 10 to form an embodiment of a catheter assembly 12. Alternate embodiments may be provided wherein the electrode is comprised of multiple members that connect or fit together to form the electrode. Various materials may be used in the formation of such electrodes, including a combination of electrically conductive materials and materials that are less thermally conductive.

In the illustrated embodiment, outer body portion 18 including outer surface 20 of electrode 10 is generally cylindrical in shape terminating in a hemispherical end. However, outer body portion 18 may be provided in alternate configurations depending on the design of the catheter assembly and the procedures being performed. Proximal portion 22 of electrode 10 is generally adjacent to catheter shaft 14, and more particularly, may be disposed on the distal end of catheter shaft 14. Distal portion 24 of electrode 10 is generally more remote from catheter shaft 14 and is the portion of electrode 10 that is placed in contact with tissue. Distal portion 24 further includes a distal end 36 which may be generally hemispherical although alternate configurations are contemplated by the present invention.

Proximal portion 22 of electrode 10 may further include a mounting portion, such as mounting shaft 34 that is provided on the proximal end 30 of electrode 10. Mounting shaft 34 may be connected to or an integral part of proximal end 30 of proximal portion 22 of electrode 10 and may be received within or connected to catheter shaft 14 of assembly 12. In an embodiment, coupling member 32 is disposed between mounting shaft 34 and catheter shaft 14. A coupling member 32, such as a seal or adhesive, is provided to ensure that electrode 10 is connected to catheter shaft 14. Coupling member 32 is generally known in the art and includes any type of material known for such a purpose to those of ordinary skill in the art. Moreover, coupling member 32 may have alternate configurations or arrangements to connect electrode 10 with catheter shaft 14.

With reference to FIG. 2, inner cavity 26 of electrode 10 includes a central longitudinal axis 38 which may extend along the length of electrode 10. Inner cavity 26 may have a generally tubular configuration, although alternate embodiments of the inner cavity may be used. Inner cavity 26 extends through proximal portion 22 and into distal portion 24 of electrode 10.

As seen in FIG. 2, electrode 10 includes at least one fluid passageway 28, such as 28a, 28b, and/or 28c. Passageway may include and be referred to as conduit(s), irrigation port(s), irrigation hole(s), channel(s), or any other type of structure used by one of ordinary skill in the art. In general, passageway 28 extends from internal cavity 26 to outer surface 20 of electrode 10. In accordance with an embodiment of the present invention, at least one passageway 28 extends to outer surface 20 towards proximal portion 22 or in a proximal direction at an angle (e.g., $\Theta_1$, $\Theta_2$) in relation to the central longitudinal axis 38. As a result, fluid flow is directed toward proximal end 22 of the electrode 10. In this embodiment, passageway 28 extends at an angle substantially less than perpendicular to the longitudinal axis 38. Angling of the passageway(s) 28 away from perpendicular, but less than parallel, further assists in the delivery of the fluid to the targeted tissue areas, further decreases the risk of coagulation of the bodily fluids during ablation procedures, and allows for improved measurement and control of electrode 10 during operation. More specifically, one or more passageways 28 may be oriented to direct irrigated fluid flow at the target area and/or region adjacent, preferably immediately adjacent, the intersection between the electrically conductive electrode 10 and electrically nonconductive catheter shaft 14. Blood coagulation is more likely to occur at or about such a target area due to a sharp rise in RF intensity, material discontinuity, and potentially geometric discontinuity caused by manufacturing imperfections in joining electrode 10 and catheter shaft 14. In some embodiments, the angle formed between passageway 28 and longitudinal axis 38 is generally less than 90 degrees and more than 5 degrees. In specific embodiments, the passageways 28 extend at an angle between 20 and 70 degrees, and may extend at an angle between 30 and 60 degrees. Angles $\Theta_1$, $\Theta_2$ may be equal to one another or may be different depending on the positioning of passageways 28 and the design of the electrode. In a further embodiment, a plurality of passageways (e.g. at least four) may be directed towards proximal portion 22 of the electrode 10. In another embodiment, up to eight fluid passageways may be provided directed towards the proximal portion of the electrode. It is also contemplated that one or more passageways may be further angled in a second dimension, such that one or more passageways are configured to provide fluid to the external portion of the assembly in a swirling, or helical fashion. Such a configuration can also serve to keep the fluid in closer proximity to the electrode assembly, thereby further preventing coagulation during operation.

In addition to fluid passageway 28 directed towards the proximal portion 22 or in a proximal direction of the assembly 10, alternate embodiments of fluid passageways may be incorporated within electrode 10. Furthermore, passageways 28 are disposed circumferentially around electrode 10, generally equidistant from one another, although alternate confirmations and placements of passageway 28 may be used depending on the design or desired performance (e.g., to cover a given volume of fluid flow) of electrode 10.

More particularly, in an alternate embodiment, a plurality of fluid passageways may be directed towards proximal portion 22 of the electrode 10. In an embodiment, as illustrated in FIG. 2, the cross-sectional view of electrode 10 shows two fluid passageways 28a extending towards proximal end 30. Passageways 28a extend from inner cavity 26 towards outer surface 20 providing an opening on outer surface 20 for the flow of fluid. Passageways 28a extend towards proximal portion 22 at angles ($\Theta_1$, $\Theta_2$) less than 90 degrees but greater than 5 degrees. As previously discussed, angles $\Theta_1$, $\Theta_2$ may be between about 30 and about 70 degrees, and may be between 30 and 60 degrees. In addition, two fluid passageways 28b and 28b extend perpendicular to the longitudinal axis 38. Another fluid passageway 28c may preferably be provided along longitudinal axis 38 at distal end 32 of distal portion 24. Each of the fluid passageways 28a-28c directs fluid from inner cavity 26 to orifices disposed on outer surface 20 of electrode 10. Different combinations of passageways in alternate configurations may be used.

The size and configuration of passageway 28 (such as 28a, 28b, and/or 28c) may vary depending on the size and design of electrode 10. In an embodiment, the diameter of passageway 28 ranges from 10-20 thousandths of an inch. In another embodiment, the diameter of the passageway 28 ranges from 12-16 thousandths of an inch. Moreover, the flow rate and/or volume of fluid flow may range from 13-20 ml/min. The diameter size of passageway 28 may be configured to permit a given flow volume or rate, and further may vary depending on the number of passageways provided by electrode 10 as well as the length on the electrode or any other feature provided by the electrode or catheter assemblies.

Figure 3A:
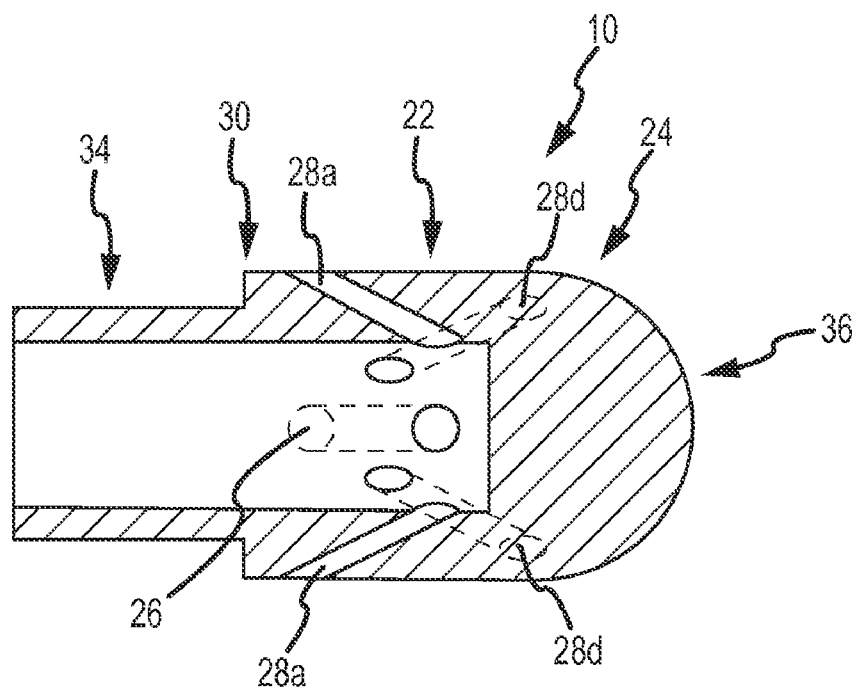
FIGS. 3A and 3B are cross-sectional views of an ablation electrode according to alternate embodiments of the present invention.
Figure 3B:
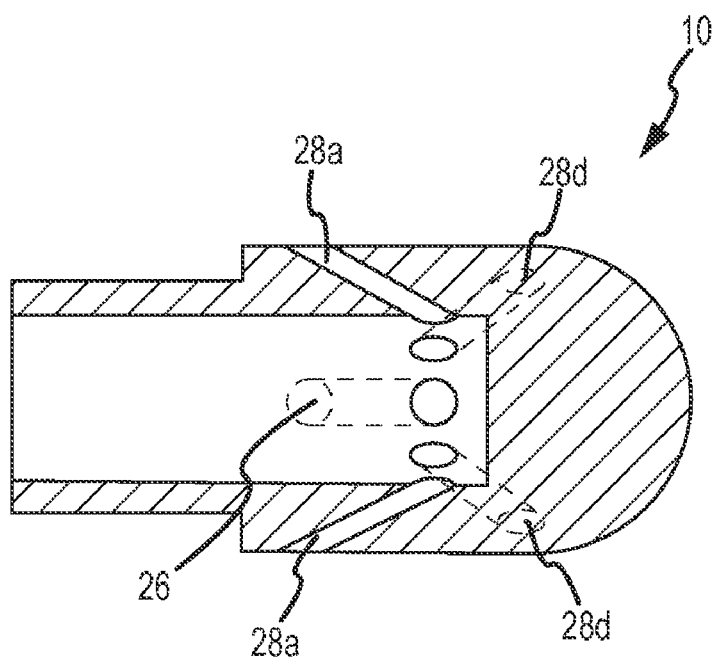

Additional alternate embodiments of the present invention may be seen in FIGS. 3A and 3B. FIG. 3A includes an electrode 10, of the type previously described, with multiple fluid passageways that provide/permit fluid flow from inner cavity 26 proximal portion 22 of electrode 10. Additional fluid passageways 28d are provided in such that the fluid flow from inner cavity 26 is directed toward distal portion 24 of electrode 10. FIG. 3B further illustrates an embodiment, wherein passageways 28a and 28d (shown in phantom) at least partially intersect or overlap with one another within electrode 10, therein providing passageways 28 in cross-arrangement with one another. This type of configuration may be used, for example, when an increased number of passageways are used or there is limited space on the outer surface of the electrode.

In addition to the various passageways configurations, electrode 10 may include additional components, such as those typically used by ablation electrodes, including but not limited to temperature (thermal) sensors, pressure sensors, and/or power wire.

Figure 4:
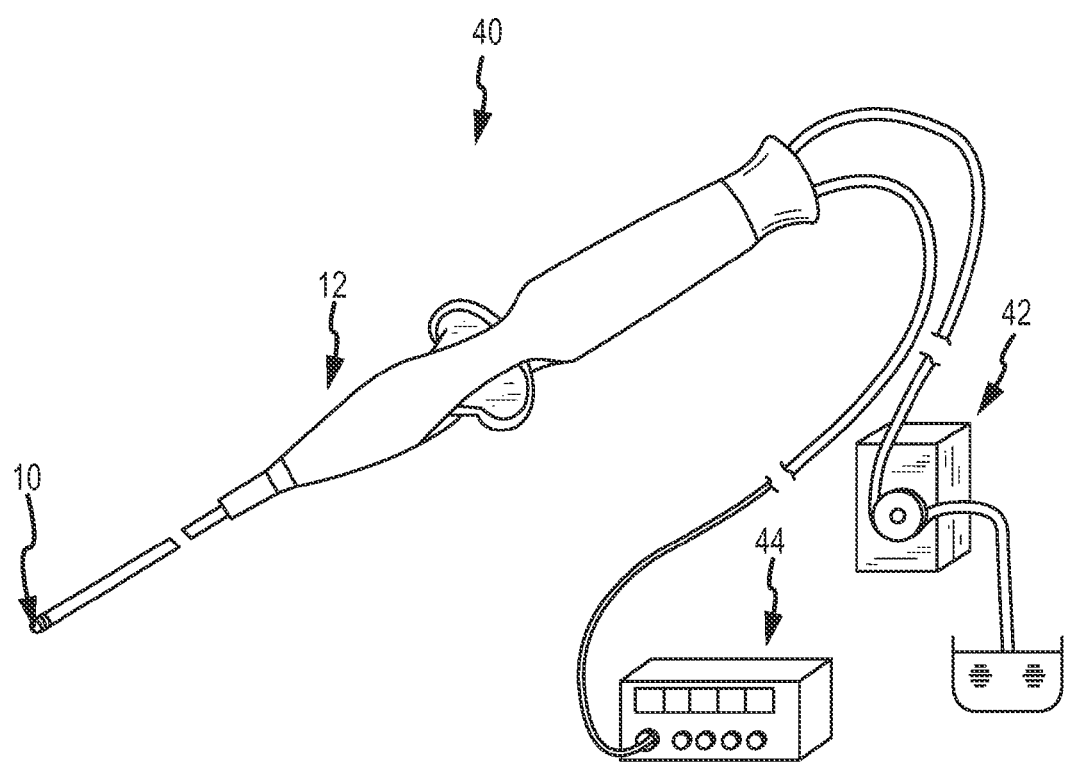
FIG. 4 is an isometric view of an ablation catheter system according to an embodiment of the present invention including an irrigated ablation electrode in conjunction with an irrigated catheter assembly operably connected to an energy source and a fluid source.

As generally shown in the embodiment illustrated in FIG. 4, the ablation electrode 10 may comprise part of an irrigated ablation catheter assembly 12. The catheter assembly may be operably connected to a fluid source 42, such as a pump assembly, and an energy source 44, such as an RF generator assembly, together comprising an embodiment of a catheter system 40. The fluid source 42 and energy source 44 may serve to facilitate the operation of ablation procedures and may involve monitoring any number of chosen variables (e.g. temperature of ablation electrode, ablation energy, and position of the assembly), assisting in manipulation of the assembly during the use, and providing the requisite energy source delivered to the electrode 10. Furthermore, additional components may be integrated into the system, such as visualization, mapping and navigation components known in the art, including among other things, NavX® or other systems.

The general structural and functional features of catheter systems such as those generally comprising catheter assembly 12 are well-known to those of skill in the art. For example, the fluid source 42 can comprise various known assembly, including fixed volume rolling pumps, variable volume syringe pumps and other pump assembly known to those skill in the art. Moreover, the fluid provided by fluid source, may comprise a suitable biocompatible fluid, such as saline. The energy source 44 may comprise an IBI-1500T RF Cardiac Ablation Generator available from Irvine Biomedical, Inc. The energy source can also comprise various other known energy sources. Accordingly, the various alternate embodiments of the present invention may be included within catheter system 40.

Although a number of embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An ablation electrode for use with an irrigated ablation catheter assembly comprising:
   an outer body portion including an outer surface, a proximal portion with a proximal end and a distal portion with a distal end;
   an inner cavity defined within the outer body portion, the inner cavity including a central longitudinal axis;
   a first passageway that extends from the inner cavity to the outer surface towards the proximal end of the electrode at a first acute angle with respect to the central longitudinal axis; and
   a second passageway that extends from the inner cavity to the outer surface towards the distal end of the electrode at a second acute angle with respect to the central longitudinal axis;
   wherein the first passageway and the second passageway axially overlap.

2. The ablation electrode of claim 1, wherein the outer surface of the proximal portion and a catheter shaft meet at an intersection, and the first passageway is configured to direct fluid flow through the first passageway toward a region adjacent the intersection.

3. The ablation electrode of claim 1, wherein the electrode comprises a plurality of passageways extending from the inner cavity to the outer surface towards the proximal end of the electrode.

4. The ablation electrode of claim 3, wherein the passageways that extend towards the proximal end of the electrode are disposed equidistant about the outer body portion of the electrode.

5. The ablation electrode of claim 1, wherein the inner cavity is cylindrical about the longitudinal axis.

6. The ablation electrode of claim 5, wherein at least one of the first acute angle and the second acute angle is between about 30 and about 70 degrees.

7. The ablation electrode of claim 1, wherein the inner cavity is in fluid communication with at least one of the passageways extending to the outer surface of the electrode.

8. The ablation electrode of claim 1, wherein at least one of the first acute angle and the second acute angle is between about 30 and about 70 degrees.

9. The ablation electrode of claim 1, wherein the first passageway meets the inner cavity at a first outlet and the second passageway meets the inner cavity at a second outlet, the first outlet being disposed axially distal of the second outlet.

10. An ablation catheter assembly comprising:
an electrode having an outer body portion including an outer surface, a proximal portion with a proximal end and a distal portion with a distal end, an inner cavity defined within the outer body portion, the inner cavity including a central longitudinal axis, a first passageway that extends from the inner cavity to the outer surface towards the proximal end of the electrode at a first acute angle with respect to the central longitudinal axis, and a second passageway that extends from the inner cavity to the outer surface towards the distal end of the electrode at a second acute angle with respect to the central longitudinal axis, wherein the first passageway and the second passageway axially overlap; and
a catheter shaft having a proximal end and a distal end, wherein the outer surface of the proximal portion and the catheter shaft meet at an intersection, and the first passageway is configured to direct fluid flow through the first passageway toward a region adjacent the intersection.

11. The catheter assembly of claim 10, wherein the electrode comprises a plurality of passageways extending from the inner cavity to the outer surface towards the proximal end of the electrode.

12. The catheter assembly of claim 10, wherein the inner cavity is in fluid communication with at least one of the passageways extending to the outer surface of the electrode.

13. The catheter assembly of claim 10, wherein the first acute angle formed by the first passageway extending from the inner cavity towards the proximal end is between about 30 and about 70 degrees.

14. The catheter assembly of claim 10, wherein the acute angle formed by the second passageway extending from the inner cavity to the outer surface towards the distal end is between about 30 and about 70 degrees.

15. The ablation electrode of claim 10, wherein the first passageway meets the inner cavity at a first outlet and the second passageway meets the inner cavity at a second outlet, the first outlet being disposed axially distal of the second outlet.

16. An ablation system comprising:
a catheter assembly including:
an electrode having a proximal portion with a proximal end and a distal portion with a distal end, and
a catheter shaft including a proximal end and a distal end;
a fluid source configured to be connected to the catheter assembly; and
an energy source configured to be connected to the catheter assembly;
wherein the electrode has an outer body portion, including an outer surface, an inner cavity defined within the outer body portion, the inner cavity including a central longitudinal axis, a first passageway that extends from the inner cavity towards the proximal end of the electrode at a first acute angle with respect to the central longitudinal axis, and a second passageway that extends from the inner cavity towards the distal end of the electrode at a second acute angle with respect to the central longitudinal axis, wherein the first passageway and the second passageway axially overlap;
further wherein the distal end of the catheter shaft is configured to be connected to the electrode.

17. The ablation electrode of claim 16, wherein the first passageway meets the inner cavity at a first outlet and the second passageway meets the inner cavity at a second outlet, the first outlet being disposed axially distal of the second outlet.

* * * * *